United States Patent
Kim

(10) Patent No.: US 8,215,152 B2
(45) Date of Patent: Jul. 10, 2012

(54) TESTING AN ACOUSTIC PROPERTY OF AN ULTRASOUND PROBE

(75) Inventor: Jin Ki Kim, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 457 days.

(21) Appl. No.: 12/622,240

(22) Filed: Nov. 19, 2009

(65) Prior Publication Data

US 2010/0122566 A1 May 20, 2010

(30) Foreign Application Priority Data

Nov. 19, 2008 (KR) .................. 10-2008-0115311

(51) Int. Cl.
 *G01N 29/30* (2006.01)
(52) U.S. Cl. ........... 73/1.83; 73/1.82; 702/116; 702/126
(58) Field of Classification Search ............ 73/1.79,
  73/1.82–1.83; 250/252.1; 356/243.1, 518,
  356/932, FOR. 124; 367/13; 702/94, 103,
  702/116, 124, 126, 191, FOR. 166
 See application file for complete search history.

(56) References Cited

U.S. PATENT DOCUMENTS

| | | | | |
|---|---|---|---|---|
| 2,723,556 A | * | 11/1955 | Willard | 73/597 |
| 4,081,216 A | * | 3/1978 | Cook | 73/1.83 X |
| 5,230,339 A | * | 7/1993 | Charlebois | 73/1.82 X |
| 5,463,593 A | | 10/1995 | Zanelli et al. | |
| 5,532,973 A | * | 7/1996 | Zehner | 367/13 |
| 5,886,245 A | * | 3/1999 | Flax | 73/1.83 X |
| 6,760,486 B1 | * | 7/2004 | Chiao et al. | 382/274 |
| 2007/0204671 A1 | * | 9/2007 | Sliwa et al. | 73/1.83 |
| 2010/0280373 A1 | * | 11/2010 | Fan et al. | 600/439 |

FOREIGN PATENT DOCUMENTS

| | | | | |
|---|---|---|---|---|
| EP | 272347 A1 | * | 6/1988 | 367/157 |
| JP | 2001-281047 | | 10/2001 | |
| JP | 2005342140 A | * | 12/2005 | |
| JP | 2009030996 A | * | 2/2009 | |
| KR | 10-2007-0002131 | | 1/2007 | |

OTHER PUBLICATIONS

Korean Office Action issued in Korean Patent Application No. 10-2008-0115311, mailed Feb. 25, 2011, in Korean, 4 pages.

* cited by examiner

*Primary Examiner* — Thomas P Noland

(74) *Attorney, Agent, or Firm* — McDermott Will & Emery LLP

(57) ABSTRACT

Embodiments for testing an acoustic property of an ultrasound probe including a plurality of transducer elements are disclosed. A Schlieren image of an ultrasound probe and a visualized acoustic field of an ultrasound signal generated when one of the transducer elements is excited are acquired. A preprocessing including noise removal and position calibration upon the Schlieren image is then carried out. An acoustic property of the ultrasound probe is tested based on the preprocessed Schlieren image.

6 Claims, 3 Drawing Sheets

TESTING AN ACOUSTIC PROPERTY OF AN ULTRASOUND PROBE

The present application claims priority from Korean Patent Application No. 10-2008-0115311 filed on Nov. 19, 2008, the entire subject matter of which is incorporated herein by reference.

TECHNICAL FIELD

The present disclosure generally relates to testing systems, and more particularly to a system and method of testing an acoustic property of an ultrasound probe.

BACKGROUND

An ultrasound diagnostic system has become an important and popular diagnostic tool since it has a wide range of applications. Specifically, due to its non-invasive and non-destructive nature, the ultrasound diagnostic system has been extensively used in the medical profession. Modern high-performance ultrasound diagnostic systems and techniques are commonly used to produce two or three-dimensional diagnostic images of internal features of an object (e.g., human organs).

A diagnostic ultrasound system generally uses an ultrasound probe containing an array of transducer elements, which may be formed by piezoelectric materials, to transmit and receive ultrasound signals. The ultrasound diagnostic system electrically excites transducer elements to generate ultrasound signals that travel into the body. Echoes reflected from tissues and organs return to the transducer elements and are converted into electrical signals. An ultrasound image is formed by processing the electrical signals outputted from the transducer elements. Thus, an acoustic property of the ultrasound probe is very important to form an accurate ultrasound image.

A hydrophone has been traditionally used to test the acoustic property of the ultrasound probe such as a beam profile, an acceptance angle and the like. In such a case, approximately 4 to 5 hours are required to test the beam profile and the acceptance angle for each of the transducer elements included in the ultrasound probe. Further, an extra device for automatically controlling a position of the hydrophone is required to accurately test the acoustic property of the ultrasound probe. Additionally, when a needle-type hydrophone is adopted to test the acoustic property of the ultrasound probe, the hydrophone may be inevitably positioned within a sound field, which may affect a free field condition. Thus, a distorted acoustic property may be obtained. Also, a response property of the hydrophone itself may cause the acoustic property to be distorted.

Recently, a method of using a Schlieren system has been utilized as a faster technique to test the acoustic property of the ultrasound probe. The Schlieren system is a system for visualizing an acoustic field of the ultrasound signals by using a characteristic of the light in which its refractive index varies according to density variation of the ultrasound signals in a transmission medium (e.g., water). This method of using the Schlieren system may perform the test faster than the hydrophone-based method. The Schlieren system is typically configured with a water tank for containing water as the transmission medium of the ultrasound signals, a plurality of lenses for collimating and focusing the light and the like. Thus, when the water tank or the lenses are contaminated, the Schlieren system may not acquire a Schlieren image, which is noise free, due to the contamination. This makes it difficult to accurately detect the acoustic property.

SUMMARY

Embodiments for testing an acoustic property of an ultrasound probe including a plurality of transducer elements are disclosed herein. In one embodiment, by way of non-limiting example, a system for testing an acoustic property of an ultrasound probe including a plurality of transducer elements, comprises: an image acquisition unit configured to acquire a Schlieren image of an ultrasound probe and a visualized acoustic field of an ultrasound signal generated when one of the transducer elements is excited; and an acoustic property testing unit configured to perform preprocessing including noise removal and position calibration upon the Schlieren image, and test an acoustic property of the ultrasound probe based on the preprocessed Schlieren image.

In another embodiment, a method of testing an acoustic property of an ultrasound probe including a plurality of transducer elements, comprises: a) exciting one of the transducer elements to generate an ultrasound signal; b) acquiring a Schlieren image of the ultrasound probe and a visualized acoustic field of the ultrasound signal; c) performing preprocessing including noise removal and position calibration upon the Schlieren image; and d) testing an acoustic property of the ultrasound probe based on the preprocessed Schlieren image.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
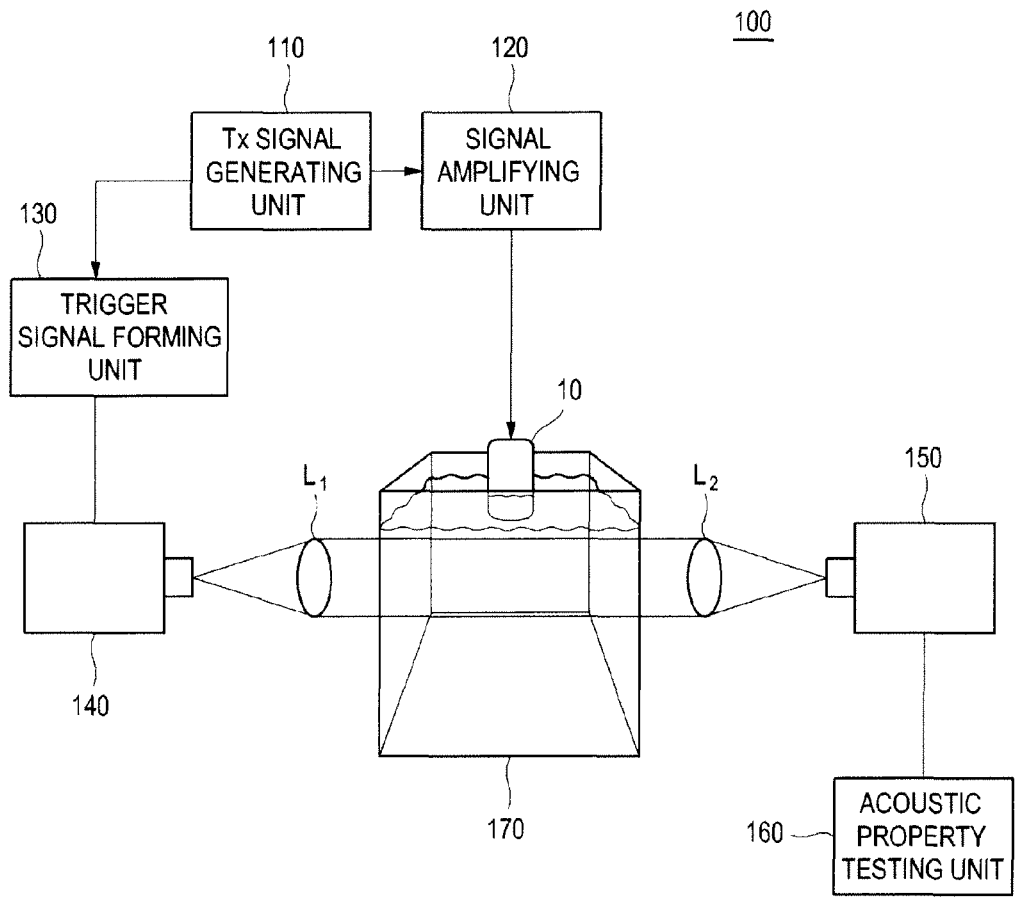
FIG. 1 is a schematic diagram showing an illustrative embodiment of a system for testing an acoustic property of an ultrasound probe.

FIG. 1 is a schematic diagram showing an illustrative embodiment of a system for testing an acoustic property of an ultrasound probe. As depicted therein, the testing system 100 may include an ultrasound probe 10 for transmitting an ultrasound beam. The ultrasound probe 10 may include a plurality of transducer elements for converting electrical pulse signals into ultrasound signals and vice-versa. In one embodiment, the ultrasound probe 10 may be operable to transmit the ultrasound beam, while a face of the ultrasound probe 10 is sunk under water contained in a water tank 170.

The testing system 100 may further include a transmit (Tx) signal generating unit 110. The Tx signal generating unit 110 may be operable to generate a Tx signal. In one embodiment, the Tx signal may be transmitted to one of the transducer elements. That is, one transducer element may be excited in response to the Tx signals to thereby generate an ultrasound signal.

The testing system 100 may further include a signal amplifying unit 120. The signal amplifying unit 120 may be configured to amplify the Tx signal at a predetermined level. The amplified Tx signal is transmitted to one of the transducer elements of the ultrasound probe 10.

The testing system 100 may further include a trigger signal generating unit 130. The trigger signal generating unit 130 may be operable to generate a trigger signal based on the Tx signals. In one embodiment, the trigger signal may be generated by delaying the Tx signals by a predetermined time duration.

The testing system 100 may further include a light firing unit 140. The light firing unit 140 may include a light source such as a laser source, which fires whenever it is triggered by the trigger signal. The light source may fire a laser beam into the water tank 170 through a first lens L1. The first lens L1 may be used to collimate the laser beam.

The testing system 100 may further include an image acquisition unit 150. The image acquisition unit 150 may be configured to receive a laser beam through a second lens L2. The second lens L2 may be used to focus the laser beam transmitted through the water tank 170. In one embodiment, the image acquisition unit 150 may include a video camera (not shown), such as a low noise camera, and a frame grabber (not shown). The video camera may be configured to form an image signal in response to the received laser beam. The video camera may include a CMOS image sensor, a CCD image sensor or the like. The frame grabber may be operable to form a Schlieren image by using the image signal.

The testing system 100 may further include an acoustic property testing unit 160. The acoustic property testing unit 160 may be configured to analyze the Schlieren image provided by the image acquisition unit 150 to test the acoustic property of the ultrasound probe 10. The acoustic property testing unit 160 may further be operable to output a test result.

Figure 2:
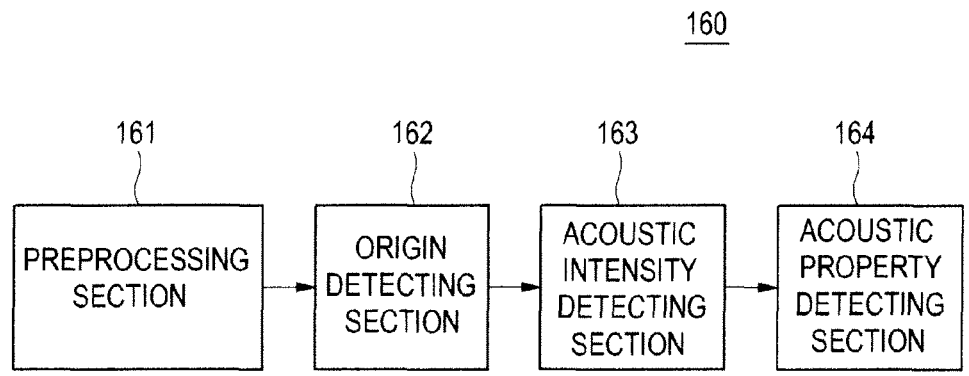
FIG. 2 is a block diagram showing an illustrative embodiment of an acoustic property testing unit.

FIG. 2 is a block diagram showing an illustrative embodiment of the acoustic property testing unit 160. Referring to FIG. 2, the acoustic property testing unit 160 may include a preprocessing section 161, an origin detecting section 162, an acoustic intensity detecting section 163 and an acoustic property detecting section 164.

Figure 3:
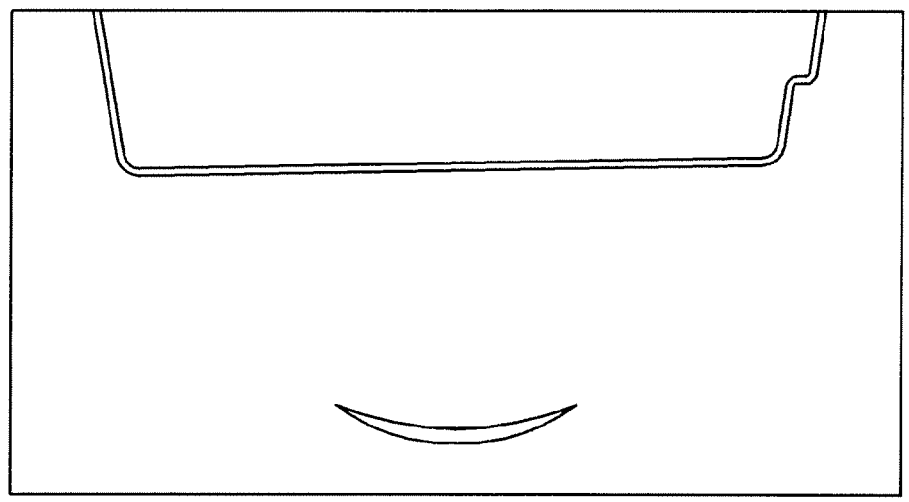
FIG. 3 is a schematic diagram showing an example of a Schlieren image.
Figure 4:
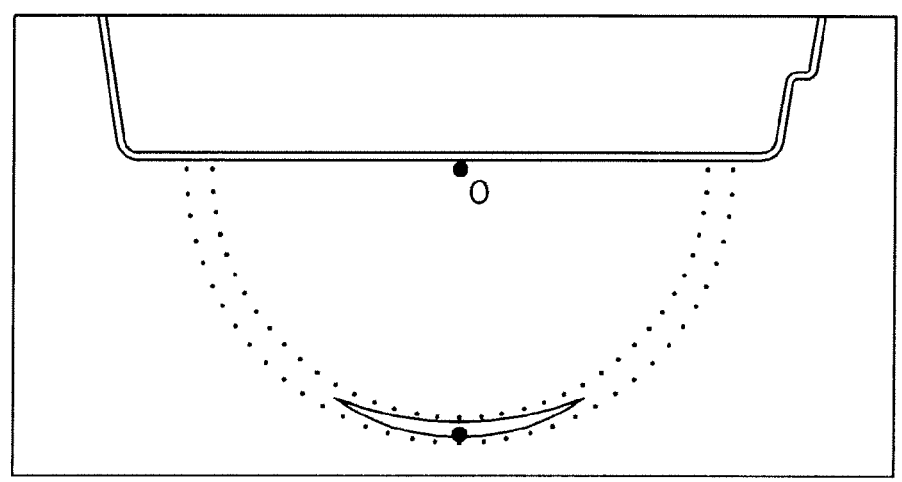
FIG. 4 is a schematic diagram showing an example of a preprocessed Schlieren image.

The preprocessing section 161 may be operable to perform preprocessing upon the Schlieren image provided from the image acquisition unit 150. In one embodiment, the preprocessing may include noise removal processing for removing noises from the Schlieren image and/or position calibration processing for calibrating a position of the ultrasound probe in the Schlieren image. Noises caused by contaminations of the water tank 170, lenses $L_1$ and $L_2$, etc. may exist. Further, the ultrasound probe may be angled in a counter clockwise direction in the Schlieren image 211, as illustrated in FIG. 3. The preprocessing may be operable to perform the noise removal processing upon the Schlieren image 211 to remove the noise therefrom. The preprocessing may further be operable to detect the ultrasound probe image in the Schlieren image 211 and determine whether the front surface of the ultrasound probe is aligned in parallel in the Schlieren image. In one embodiment, by way of non-limiting example, determining the alignment status of the ultrasound probe may involve the edge detection for detecting edges of the ultrasound probe and slope detection for detecting slopes of the detected edges. The preprocessing section 161 may further be operable to calibrate the position of the ultrasound probe in the Schlieren image based on the determination result, as illustrated in FIG. 4. The preprocessing section 161 may be configured to output the preprocessed Schlieren image 212.

The origin detecting section 162 may be operable to detect the excited one of the transducer elements, which is transmitting, on the preprocessed Schlieren image 212. In one embodiment, the origin detecting section 162 may be operable to detect the excited transducer element by using brightness values in the Schlieren image. For example, a pixel having the highest brightness value in the Schlieren image may be detected as the excited transducer element. Further, the position of the detected excited transducer element may be set as the origin O in the Schlieren image. However, the detection may not be limited thereto. The excited transducer element may be detected by using various methods, which are well known to a person skilled in the art.

The acoustic intensity detecting section 163 may be operable to detect acoustic intensities at each predetermined azimuth with respect to the origin O on the Schlieren image. The acoustic intensities may be detected by utilizing the characteristics of the acoustic intensities, which are proportional to brightness values on the Schlieren image.

Figure 5:
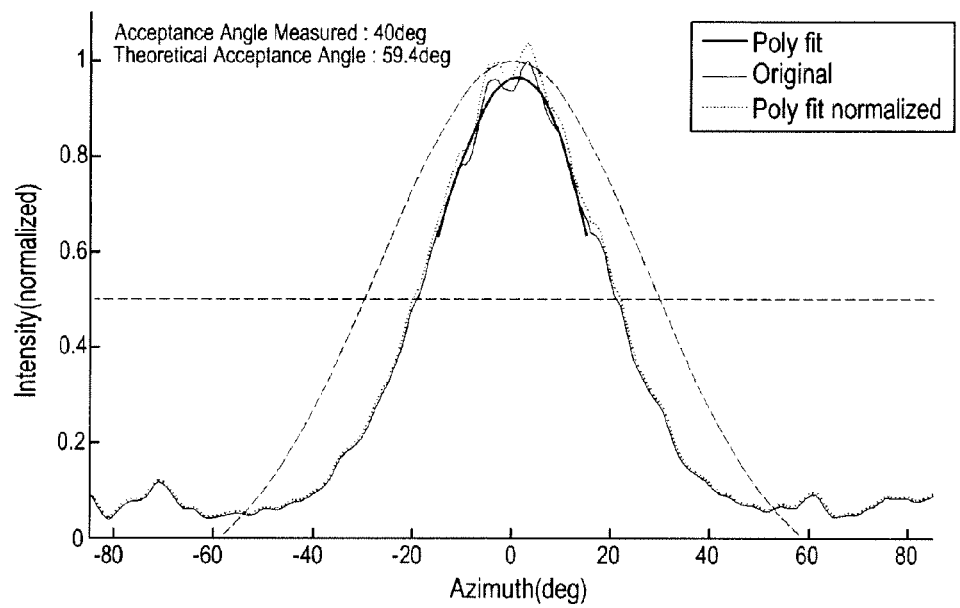
FIGS. 5 and 6 are graphs showing beam profiles detected from a preprocessed Schlieren image.
Figure 6:
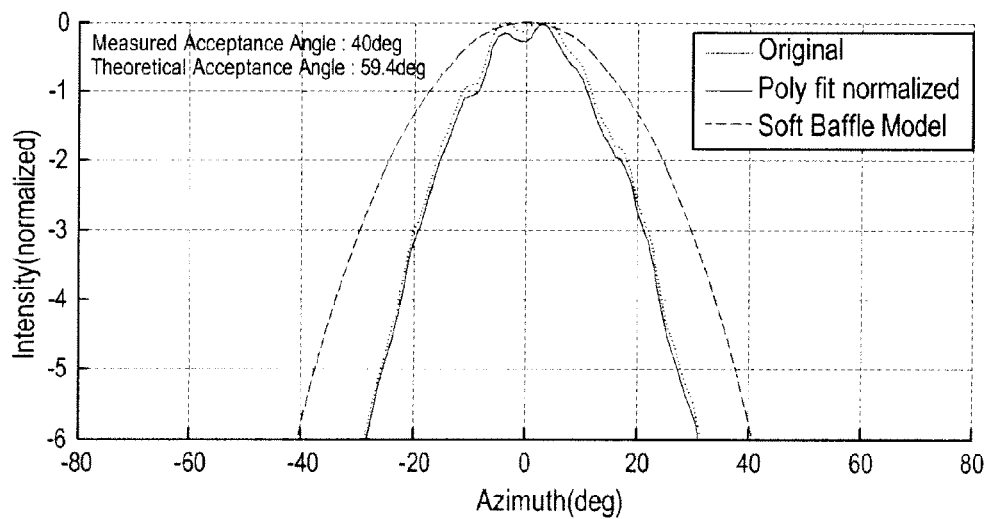

The acoustic property detecting section 164 may be operable to detect an acoustic property of the ultrasound probe 10, e.g., a beam profile and an acceptance angle thereof based on the acoustic intensities detected in the acoustic intensity detecting section 163. In one embodiment, the acoustic property detecting section 164 may be operable to detect the beam profile by using the acoustic intensities detected at each predetermined azimuth, as shown in FIGS. 5 and 6. The detection of the beam intensity profile may be performed by using methods, which are well known to a person skilled in the art. Thus, detailed description thereof will be omitted herein. FIG. 5 shows a graph of a beam intensity profile with respect to azimuth, wherein the intensity is indicated in a linear scale. FIG. 6 shows a graph of a beam intensity profile with respect to azimuth, wherein the intensity is indicated in a dB scale. As shown in FIGS. 5 and 6, the acoustic intensity is at maximum around the azimuth of 0 degree with respect to the origin O (i.e., at a main direction of the ultrasound beam), and the acoustic intensity decreases as the azimuth increases. In FIGS. 5 and 6, the dotted lines represent theoretical values, which are assumed by the Soft baffle model. Further, the acoustic property detecting section 164 may be operable to detect acceptance angles corresponding to a plurality of intensities according to the maximum acoustic intensity. That is, the acoustic property detecting section 164 may be operable to detect the acceptance angles corresponding to the intensities ranging from −1 dB to −6 dB.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A system for testing an acoustic property of an ultrasound probe including a plurality of transducer elements, comprising:
an image acquisition unit configured to acquire a Schlieren image of the ultrasound probe and a visualized acoustic field of an ultrasound signal generated when one of the transducer elements is excited; and
an acoustic property testing unit configured to perform preprocessing including noise removal and position calibration upon the Schlieren image, and test an acoustic property of the ultrasound probe based on the preprocessed Schlieren image.

2. The system of claim 1, wherein the acoustic property includes a beam profile and an acceptance angle.

3. The system of claim 2, wherein the acoustic property testing unit includes:
a preprocessing section configured to perform the preprocessing upon the Schlieren image;
an origin detecting section configured to detect a location of an excited transducer element in the Schlieren image and set the detected location as an origin;
an acoustic intensity detecting section configured to detect acoustic intensities at each predetermined azimuth with respect to the origin in the Schlieren image; and
an acoustic property detecting section configured to detect the beam profile and the acceptance angle based on the detected acoustic intensities.

4. A method of testing an acoustic property of an ultrasound probe including a plurality of transducer elements, comprising:
a) exciting one of the transducer elements to generate an ultrasound signal;
b) acquiring a Schlieren image of the ultrasound probe and a visualized acoustic field of the ultrasound signal;
c) performing preprocessing including noise removal and position calibration upon the Schlieren image; and
d) testing an acoustic property of the ultrasound probe based on the preprocessed Schlieren image.

5. The method of claim 4, wherein the acoustic property includes a beam profile and an acceptance angle.

6. The method of claim 5, wherein the d) includes:
detecting a location of the excited transducer element in the Schlieren image;
setting the detected location as an origin;
detecting acoustic intensities at each predetermined azimuth with respect to the origin in the Schlieren image; and
detecting the beam profile and the acceptance angle based on the detected acoustic intensities.

* * * * *